United States Patent [19]

Magee

[11] Patent Number: 4,511,735

[45] Date of Patent: Apr. 16, 1985

[54] PARTICULATE FUNGICIDES

[75] Inventor: Philip S. Magee, Vallejo, Calif.

[73] Assignee: Chevron Research Company, San Francisco, Calif.

[21] Appl. No.: 537,753

[22] Filed: Sep. 30, 1983

[51] Int. Cl.³ .............. C07C 143/74; C07C 143/76; C07C 143/78

[52] U.S. Cl. .................... 514/601; 564/85; 564/95; 564/96; 564/97; 564/99; 564/98; 71/3; 514/605

[58] Field of Search .............. 564/95, 85, 96, 97, 564/98, 99; 424/321

[56] References Cited

U.S. PATENT DOCUMENTS

| | | | |
|---|---|---|---|
| 3,412,149 | 11/1968 | Schlör et al. | 564/85 |
| 3,703,500 | 11/1972 | Nast et al. | 564/97 X |
| 3,927,090 | 12/1975 | Goralski et al. | 564/97 |
| 4,068,000 | 1/1978 | Edwards | 564/97 X |
| 4,085,093 | 4/1978 | Hopper | 564/98 X |
| 4,208,348 | 6/1980 | Chan | 564/98 X |
| 4,402,980 | 9/1983 | Kühle et al. | 564/98 X |

Primary Examiner—Paul F. Shaver
Attorney, Agent, or Firm—S. R. LaPaglia; T. G. DeJonghe; S. L. Biggs

[57] ABSTRACT

The present invention relates to novel fungicides of the formula:

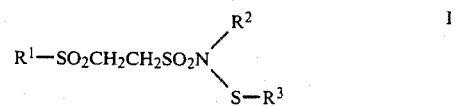

wherein $R^1$ is lower alkyl, lower akenyl, lower alkynyl or aryl of 6 to 10 carbon atoms optionally substituted with up to 3 halogen atoms; $R^2$ is lower alkyl, lower alkenyl, lower alkynyl or aryl of 6 to 10 carbon atoms optionally substituted with up to 3 halogen atoms or up to 3 lower alkoxy groups; and $R^3$ is alkyl of 1 to 3 carbon atoms substituted with 3 to 6 halogen atoms or trihalovinyl.

21 Claims, No Drawings

PARTICULATE FUNGICIDES

BACKGROUND OF THE INVENTION

The present invention relates to novel fungicidal N-polyhaloalkyl- or vinyl-thio substituted-ethanesulfonamide compounds.

Certain trichloromethane sulfenic acid derivatives, N-polyhaloalkylthio compounds and N-polyhaloalkylthio, N-aryl-substituted sulfonamides have pesticidal activity including activity as fungicides and insecticides. (See e.g. U.S. Pat. Nos. 2,779,788; 2,779,941; 3,178,447; 4,068,000; 4,092,429; and 4,350,831.) However, many of such compounds have severe toxicity problems, especially with regard to skin toxicity (and thus irritation) which greatly limits their usefulness due to problems associated with their application and handling.

SUMMARY OF THE INVENTION

The present invention relates to novel fungicides of the formula:

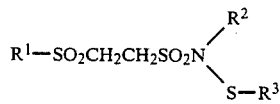

wherein $R^1$ is lower alkyl, lower alkenyl, lower alkynyl or aryl of 6 to 10 carbon atoms optionally substituted with up to 3 halogen atoms; $R^2$ is lower alkyl, lower alkenyl, lower alkynyl or aryl of 6 to 10 carbon atoms optionally substituted with up to 3 halogen atoms or up to 3 lower alkoxy groups; and $R^3$ is alkyl of 1 to 3 carbon atoms substituted with 3 to 6 halogen atoms or trihalovinyl.

Among other factors, the present invention is based on my finding that the compounds of this invention are surprisingly effective as fungicides; these compounds show surprisingly good activity in controlling a variety of plant fungal diseases.

In particular, I have found that some of these compounds have surprisingly higher melting points and reduced solubility in common organic solvents than one would expect with compounds containing a tetrachloroethylsulfenyl (TES) group or a perchloromethanesulfenyl (PMM) group of similar molecular weight. This unexpectedly higher melting point and reduced solubility is expected to improve the compounds' fungicidal utility, and, thus, should decrease phytotoxicity when applied to plants and should also increase persistence of the compound, thus make it more resistant to weathering. Other TES or PMM-containing compounds of similar molecular weight are oils or low-melting solids, rather than high-melting solids and are also more oil-soluble, properties often leading to phytotoxicity when such compounds are applied to plants.

Preferred $R^1$ groups include lower alkyl and aryl groups. Especially preferred $R^1$ groups include methyl and tert-butyl.

Preferred $R^2$ groups include lower alkyl, lower alkenyl and aryl groups. Especially preferred $R^2$ groups include methyl and phenyl.

Preferred $R^3$ groups include those where the halogen substituents are chlorine, and include, for example, trichloromethyl, 1,1,2,2-tetrachloroethyl, 1,1,1-tetrachloroethyl and trichlorovinyl. Especially preferred $R^3$ groups include 1,1,2,2-tetrachloroethyl.

DEFINITIONS

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group $-(CH_2)_m-$ wherein m is an integer greater than zero. Typical alkylene groups include methylene, ethylene, propylene and the like.

The term "alkenyl" refers to unsaturated alkyl groups having a double bond [e.g., $CH_3C=H(CH_2)_2-$] and includes both straight- and branched-chain alkenyl groups. "Lower alkenyl" refers to groups having a total of from 3 to 6 carbon atoms. Typical lower alkenyl groups include, for example, propenyl, but-3-enyl, hex-4-enyl, 2-methylpent-4-enyl, and the like.

The term "alkynyl" refers to unsaturated alkyl groups having a triple bond [e.g., $CH_3C\equiv C-(CH_2)_2-$] and includes both straight-chain and branched-chain alkynyl groups. "Lower alkynyl" refers to groups having a total of from 3 to 6 carbon atoms and includes, for example, propargyl, but-3-ynyl, hex-4-ynyl, 2-methylpent-4-ynyl and the like.

The term "halo" or "halogen" refers to the groups fluoro, chloro and bromo.

The term "alkoxy" refers to the group R'O— wherein R' is alkyl. The term "lower alkoxy" refers to alkoxy groups having from 1 to 6 carbon atoms; examples include methoxy, ethoxy, hexoxy, and the like.

The term "aryl" refers to aryl groups optionally substituted with 1 or more lower alkyl groups having a total of from 6 to 10 carbon atoms and includes, for example, phenyl, m-methylphenyl, p-butylphenyl, and naphthyl.

The term "alkylthio" refers to the group R'S— where R' is alkyl. The term "lower alkylthio" refers to alkylthio groups having from 1 to 6 carbon atoms; examples include methylthio, ethylthio, tert-butylthio, hexylthio, and the like.

The term "TES" or "tetrachloroethylsulfenyl" refers to the group tetrachloroethylthio, that is an ethylthio group in which four of the hydrogens of the ethyl ($-CH_2CH_3$) moiety have been replaced with chlorine atoms to give a tetrachloroethyl group and includes 1,1,2,2-tetrachloroethylthio, 1,1,1,2-tetrachloroethylthio and 1-fluoro-1,1,2,2-tetrachloroethylthio groups.

The term "PMM", "perchloromethyl mercaptan" or "perchloromethanesulfenyl" refers to the group trichloromethylthio, that is a methylthio group in which the three hydrogens on the methyl ($-CH_3$) moiety have been replaced with chlorine atoms.

DETAILED DESCRIPTION OF THE INVENTION

The compounds of the present invention are prepared according to the following reaction scheme:

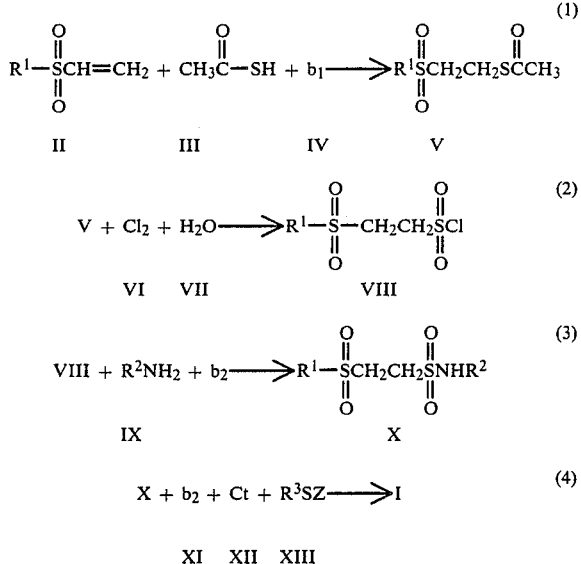

wherein $R^1$, $R^2$ and $R^3$ are as previously defined in conjunction with Formula I; $b_1$ and $b_2$ are bases; Ct is a phase transfer catalyst; and Z is halogen.

Reaction (1) is conducted by adding an approximately equimolar amount of III to a stirred mixture of II and a catalytic amount of IV in solvent. Suitable bases $b_1$ include inorganic and organic bases such as sodium methoxide, sodium hydroxide, bases such as triethyl amine, dimethylaniline, and the like. Suitable solvents include low molecular weight alcohols, such as methanol, ethanol, isopropanol, and the like. The reaction is conducted at a temperature of about 20° C. to about 35° C., or for convenience at ambient temperature, and is generally complete within about 1 to about 8 hours. Since the addition of IV is exothermic, it may be desired to cool the reaction mixture at intervals during the addition. The product V is isolated by conventional procedures such as stripping, crystallization, filtration, and the like.

Reaction (2) is conducted by bubbling VI into a mixture of V and VII in solvent. It is preferred to add about 3.0 to about 4.0 equivalents VI per equivalent V and about 3.0 to about 4.0 equivalents VII per equivalent V. Suitable solvents include concentrated acetic acid. The reaction is conducted at a temperature of about 20° C. to about 75° C., or for convenience at ambient temperature, and is generally complete within about ½ to about 2 hours. The product VIII is isolated by conventional procedures such as filtration, washing, crystallization, and the like.

Reaction (3) is conducted by adding IX to VIII in solvent. It is preferred either to add an excess of IX, on the order of about 2.0 to about 3.0 equivalents IX per equivalent VIII, or alternatively if approximate equimolar amounts of VIII and IX are used, to add an equimolar amount of organic base, preferably triethylamine. The reaction is conducted at a temperature of about 0° C. to about 25° C., or, for convenience, at ambient temperature and is generally complete within about ½ to about 1 hour. Suitable solvents include inert organic solvents such as methylene chloride, chloroform, toluene, and the like. The product X is isolated by conventional procedures such as extraction, stripping, filtration, crystallization, and the like.

Reaction (4) is conducted by combining X, XI, XII and XIII in solvent. It is preferred to add XII to a mixture of X in solvent, followed by XI and XIII. Between additions, the reaction mixture may be allowed to stir for a period of time. It is preferred to use a slight excess of XI and XIII in relation to X, on the order of about 1.2 equivalents XI and XIII per equivalent X. It is preferred to use about 1 equivalent XII per equivalent X. Suitable solvents include organic solvents such as toluene, chlorobenzene, tetrachloroethane, and the like. Suitable bases, $b_2$, include strong inorganic bases such as aqueous sodium hydroxide, potassium hyroxide, and the like. Suitable phase transfer catalysts include quaternary ammonium and phosphonium salts. One such catalyst is the tricaprylyl methyl ammonium chloride sold under the trademark Aliquat ®336. The reaction is conducted at a temperature of about 20° C. to about 35° C., and is generally complete within about 2 to about 20 hours. The product, I, is isolated by conventional procedures such as filtration, washing, extraction, stripping, chromatography, and the like.

Some starting materials, II, are commercially available. Other starting materials, II, are known compounds which may be prepared from commercially available materials by methods well known to those skilled in the art. See, e.g., Examples 7 to 10.

UTILITY

The compounds of the invention are effective in controlling fungal infections in plants.

Some of the compounds of this invention are particularly effective in protecting seeds from soil borne fungi such as *Rhizoctonia solani, Pythium ultimum, Fusarium monilofroma*, and the like.

Some of the compounds of this invention are particularly effective in controlling plant fungal infections caused by organisms such as *Plasmopara yiticola*. Some of the compounds of this invention are also useful for controlling leaf blights caused by organisms such as *Phytophthora infestans conidia, Alternaria solani conidia*, and *Septoria apii*. Some of the compounds of this invention are also useful for controlling fungal infections caused by *Uromyces phaseoli tipica, Erysiphe polygoni*, and *Piricularia oryzae*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C.

to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

Example 1

Preparation of 2-(methylsulfonyl)ethyl thiolacetate

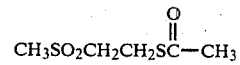

To a solution of 106 g (1.0 mole) methyl vinyl sulfone in 250 ml methanol, 1 ml triethylamine was added. Then, 76 g (1.0 mole) thioacetic acid were added dropwise in an exothermic addition. The reaction mixture was allowed to stir at ambient temperature for 4 hours. The solvent was stripped and benzene was added to chase any remaining methanol. Addition of ether to the residue, followed by cooling of the resulting mixture crystallized the above-identified product, yielding 175 g of brown solids.

Example 2

Preparation of 2-(Methylsulfonyl)ethanesulfonyl chloride

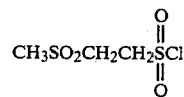

To a stirred solution of 18.2 g (0.1 mole) of 2-(methylsulfonyl)ethyl thiolacetate (the product of Example 1) in 100 ml concentrated acetic acid, 7.2 g (0.4 mole) water were added. Then chlorine gas [21.3 g (0.3 mole)] was bubbled through the reaction mixture. At the beginning of the addition of the chlorine gas there has an immediate formation of solids, but as more chlorine gas was added, the solids began to go into solution. During the addition, the temperature of the reaction mixture increased to about 60° C. By the end of the addition, everything was in solution. The reaction mixture was allowed to return to room temperature, at which point crystalline solids came out of solution. The reaction mixture was filtered, yielding 3.8 g of the above-identified product. The filtrate was poured into water and then filtered, yielding an additional 4.2 g of product.

Example 3

Preparation of N-methyl-2-(methylsulfonyl)ethanesulfonamide

To a stirred mixture of 2-(methylsulfonyl)ethanesulfonyl chloride in 50 ml chloroform, 15.5 g (0.2 mole) 40% methylamine in water were added slowly. The reaction mixture was stirred one hour and then filtered. The filtrate was washed with water. The organic phase was separated and then stripped. Cold ether was added to the residue; the resulting mixture was stirred. Filtration of the ether mixture gave 11.0 g of the above-identified product as a white solid, mp. 116°-117° C.

Elemental analysis for $C_4H_{11}NO_4S_2$ showed: calculated %C 23.40, %H 5.40, and %N 6.83; found %C 24.77, %H 5.93, and %N 7.11.

Example 4

Preparation of N-methyl, N-(1,1,2,2-tetrachloroethylsulfenyl) 2-(methylsulfonyl)ethanesulfonamide

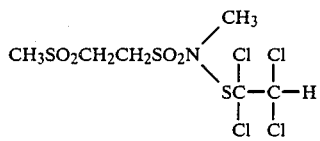

To a stirred mixture of 9.4 g (0.04676 mole) N-methyl 2-(methylsulfonyl)ethanesulfonamide (the product of Example 3) and 1.8 g Aliquat ®336 in 75 ml toluene, 4.11 g (0.051436 mole) 50% sodium hydroxide diluted with 4.1 g water were added. The resulting mixture was stirred 15 minutes. Slowly, 13.1 g (0.05611 mole) 1,1,2,2-tetrachloroethylsulfenyl chloride were added to the reaction mixture. The reaction mixture was allowed to stir overnight at room temperature. The solids were filtered, washed with water twice and then with ether. The solids were dried on filter paper to give 8.7 g of the above-identified product as a white solid, melting point 120°-123° C.

Elemental analysis for $C_6H_{11}Cl_4NO_4S_3$ showed: calculated %C 18.05, %H 2.78, and %N 3.51; found %C 18.93, %H 308, and %N 4.11.

Example 5

Preparation of N-phenyl 2-(methylsulfonyl)ethanesulfonamide

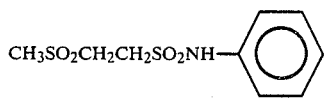

To a stirred mixture of 20.6 g (0.1 mole) 2-(methylsulfonyl)-ethanesulfonyl chloride in 100 ml methylene chloride, a homogeneous mixture of 10.2 g (0.1 mole) triethylamine and 9.3 g (0.1 mole) aniline was added dropwise, maintaining the temperature of the reaction mixture below reflux. After the addition was complete, the reaction mixture was allowed to stir two hours. The solids were filtered, washed with water twice, then with ether, and dried on filter paper to give the product as a white solid, which melted at 135° C.

Elemental analysis for $C_9H_{13}NO_4S_2$ showed: calculated %C 41.05, %H 4.95, and %N 5.32; found %C 40.7, %H 596 and %N 5.52.

Example 6

Preparation of N-phenyl,N-trichloromethanesulfenyl 2-(methylsulfonyl)ethanesulfonamide

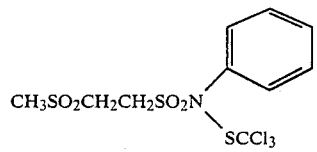

To a stirred mixture of 7.9 g (0.03 mole) N-phenyl 2-(methanesulfonyl)ethanesulfonamide (the product of Example 5) in 10 ml toluene, 1.2 g (0.03 mole) Aliquat ®336 were added, followed by 2.9 g (0.036 mole) 50% sodium hydroxide in 3 ml water. The resulting mixture was stirred overnight at room temperature. Then, 6.7 g (0.036 mole) trichloromethanesulfenyl chloride were slowly added. The reaction mixture was stirred two hours at ambient temperature. The insolubles were filtered, washed first with water, then with ether and dried on filter paper to give the first crop. The filtrate was then washed with water. The organic layer was separated, dried over magnesium sulfate, and then stripped to give the second crop. The two crops were combined to yield 2.6 g of the above-identified product as a white solid, melting point 185°-187° C. (Dec.)

Elemental analysis for $C_{10}H_{12}Cl_3NO_4S_3$ showed: calculated %C 29.09, %H 2.93, and %N 3.39; found %C 29.56, %H 2.93, and %N 3.62.

Example 7

Preparation of Tert-butylthioethanol $(CH_3)_3CSCH_2CH_2OH$

In a 2-liter flask, equipped with a thermometer, condenser and magnetic stirrer, 750 ml methanol were placed. Over a period of about 1½ hours, 46.0 g (2.0 moles) sodium metal was added at a rate slow enough so that the temperature of the methanol did not reach reflux. After the sodium addition was complete, 180.4 g (2.0 moles) tert-butyl mercaptan were added. Then, 161.0 g (2.0 moles) chloroethanol were added slowly. The reaction mixture was stirred overnight at room temperature. Solids (NaCl) came out of solution and were removed by filtration. The mixture was partially stripped. The mixture was refiltered to remove additional solids. Stripping of the filtrate gave 195 g of the above-identified product as a yellow oil.

Example 8

Preparation of Tert-butyl 2-chloroethyl sulfide $(CH_3)_3SCH_2CH_2Cl$

To a solution of 134 g (1.0 mole) tert-butylthioethanol (the product of Example 7) in 500 ml methylene chloride, 120 g (1.0 mole) thionyl chloride were slowly added in an exothermic reaction with heavy degassing. After the addition was complete, an additional 10% (12 g) thionyl chloride were added. The reaction mixture was stirred overnight at room temperature. Stripping of the solvent gave 119 g of the above-identified product as a light yellow oil.

Example 9

Preparation of tert-butyl 2-chloroethylsulfone

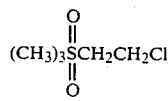

To a solution of 119.0 g (0.779 mole) tert-butyl 2-chloroethyl sulfide (the product of Example 8) in 500 ml methylene chloride cooled to −20° C., 316.2 g (1.56 moles) m-chloroperoxybenzoic acid were added slowly in portions over a period of about 30 minutes. After the addition was complete, the reaction mixture was stirred overnight at room temperature. The solids were filtered. The filtrate was treated with a saturated sodium bicarbonate solution. The layers were separated, and the organic layer was washed with a sodium bisulfite solution. The organic layer was stripped to give 90.0 g of the above-identified product as a white solid.

Example 10

Preparation of tert-butyl vinyl sulfone

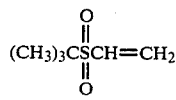

To a stirred mixture of 88.0 g (0.478 mole) tert-butyl 2-chloroethyl sulfone (the product of Example 9) in 300 ml benzene, 48.3 g (0.478 mole) triethylamine were added slowly. The reaction mixture was stirred 6 hours at ambient temperature. The mixture was filtered to remove solids, and the filtrate was stripped to give 68.0 g of the above-identified product as a white solid.

Example 11

Preparation of 2-(tert-butylsulfonyl)ethylthiolacetate

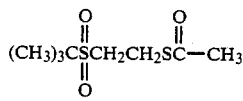

To a stirred mixture of 68.0 g (0.459 mole) tert-butyl vinyl sulfone (the product of Example 10) in 200 ml methanol, 0.5 ml triethyl amine were added; then, 34.9 g (0.459 mole) thioacetic acid were added slowly. The reaction mixture was stirred overnight at room temperature. The solvent was stripped. Cold ether was added to the residue which caused it to crystallize. The solids were filtered and dried on filter paper to give 66.0 g of the above-identified product as a white solid.

Example 12

Preparation of 2-(tert-butylsulfonyl)ethanesulfonyl chloride

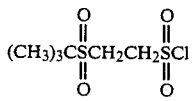

To a stirred mixture of 65.3 g (0.291 mole) 2-(tert-butylsulfonyl)ethylthioacetate (the product of Example 11) in 350 ml concentrated acetic acid 20.9 g (1.16 mole) water was added. Then, 61.8 g (0.87 mole) chlorine gas was added to the mixture by bubbling it through. At one point during the addition, the reaction mixture was almost unstirrable. During the addition, the temperature of the reaction mixture went up to 60° C. At the point where the theoretical amount of chlorine had been added (about 3 equivalents Cl₂ per equivalent thiolacetate), everything went solution, and the addition was stopped. The reaction mixture was cooled; then about 200 ml water were added. The solids were filtered, washed with ether and dried on filter paper overnight to give 68.0 g of the above-identified product.

Example 13

Preparation of N-methyl 2-(tert-butylsulfonyl)ethanesulfonamide

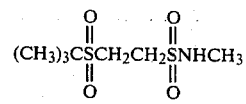

To a stirred mixture of 15.0 g (0.06 mole) 2-(tert-butyl-sulfonyl)ethanesulfonyl chloride (the product of Example 12) in 100 ml methylene chloride which had been cooled to 0° C., 9.3 g (0.12 mole) 40% methylamine in water was added dropwise in a very exothermic reaction. The reaction mixture was stirred overnight at ambient temperature. The aqueous and organic phases were separated. The organic phase was dried over magnesium sulfate, filtered and stripped to give a solid. Ether was added to the solid. The ethereal mixture was filtered and the solids dried at room temperature on filter paper to give 9.1 g of the above-identified product as a solid, melting point 119°–121° C.

Elemental Analysis for $C_7H_{17}NO_4S_2$ showed: calculated %C 34.54, %H 7.04, and %N 5.75; found %C 35.3, %H 7.21, and %N 5.71.

Example 14

Preparation of N-methyl,N-(1,1,2,2-tetrachloroethylsulfenyl)2-(tert-butylsulfonyl)ethanesulfonamide

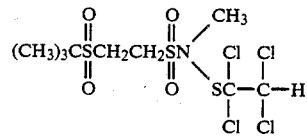

To a stirred mixture of 4.3 g (0.01767 mole) N-methyl 2-(tert-butylsulfonyl)ethanesulfonamide (the product of Example 13) in 30 ml toluene, about 0.7 g (0.001767 mole) Aliquat ® 336 (tricaprylyl methyl ammonium chloride), 1.7 g (0.0212 mole) 50% sodium hydroxide in 10 ml water were added. The resulting mixture was stirred 15 minutes at room temperature. Then, 5.0 g (0.0212 mole) 1,1,2,2-tetrachloroethylsulfenyl chloride were added with immediate exotherm and formation of solids. The reaction mixture was stirred overnight at room temperature. The solids were filtered and dried on filter paper at room temperature. The solids were dissolved in methylene chloride and chromatographed on silica gel eluting with methylene chloride to give 1.8 of the above-identified product as a white solid, melting point 151°–152° C.

Elemental analysis for $C_9H_{17}Cl_4NO_4S_3$ showed: calculated %C 24.49, %H 3.88, and %N 3.17; found %C 27.16, %H 4.09, and %N 3.31.

Example 15

Preparation of 2-(phenylsulfonyl)ethyl thiolacetate

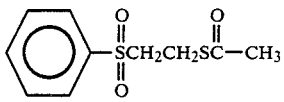

To a stirred mixture of 100 g (0.594 mole) phenyl vinyl sulfone in 250 ml methanol, 1 ml triethylamine was added. Then 45.2 g (0.594 mole) thioacetic acid was added slowly. The addition was conducted dropwise until about half of the thioacetic acid had been added; the reaction mixture was then cooled to about 30° C. and the remainder of the thioacetic acid was added in one portion. The reaction mixture was stirred at ambient temperature over the weekend. The solvent was stripped to give an oil to which ether (about 100 ml) was added. The ethereal mixture was cooled in dry ice, yielding crystals. The crystals were filtered and dried at room temperature to give the above-identified product.

Example 16

Preparation of 2-(phenylsulfonyl)ethanesulfonyl chloride

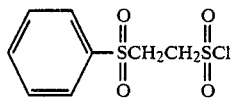

In a vessel equipped with mechanical stirrer, condenser and bubbler, 48.8 g (0.2 mole) 2-(phenylsulfonyl)ethyl thiolacetate (the product of Example 15), 14.4 g (0.8 mole) water and 300 ml concentrated acetic acid were combined. To that mixture, 42.6 g (0.6 mole) chlorine gas was added by bubbling it through the mixture. After about 10% excess chlorine gas had been added (about 4.3 g additional), the bubbler was removed, and the reaction mixture was stirred an additional hour. The solids were filtered, washed three times with ether and dried on filter paper to give 30.6 g of the above-identified product as a white solid.

Example 17

Preparation of N-methyl 2-(phenylsulfonyl)ethanesulfonamide

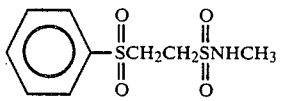

To a stirred mixture of 26.8 g (0.1 mole) 2-(phenylsulfonyl)ethanesulfonyl chloride (the product of Example 16) in 50 ml methylene chloride which had been cooled to −10° C., 15.5 g (0.2 mole) 40% methylamine (in water) was slowly added. During the addition, the temperature of the reaction mixture was not allowed to go above 10° C. After the addition was complete, the reaction mixture was allowed to stir at room temperature overnight. The solids were filtered, washed with ether several times and dried on filter paper overnight at room temperature to give 15.2 g of the above-identified product as a white solid, melting point 124°–126° C.

Elemental analysis for $C_9H_{13}NO_4S_2$ showed: calculated %C 41.05, %H 4.97, and %N 5.32; found %C 41.41, %H 5.35, and %N 5.45.

Example 18

Preparation of N-methyl, N-(1,1,2,2-tetrachloroethylsulfenyl)2-(phenylsulfonyl)ethanesulfonamide

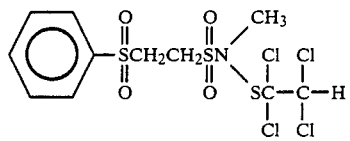

To a stirred mixture of 6.0 g (0.0228 mole) N-methyl(2-phenylsulfonyl)ethanesulfonamide (the product of Example 17) in 10 ml toluene, 1.0 g (0.00228 mole) Aliquat ® 336 (Tricaprylyl methyl ammonium chloride) was added, followed by 2.2 g (0.02736 mole) 50% sodium hydroxide and 3 ml water. The resulting mixture was stirred at room temperature overnight. Then, 6.4 g (0.02736 mole) tetrachloroethylsulfenyl chloride was added in portions. The reaction mixture was allowed to stir for two hours. The solids were filtered, washed first with water and then dried at room temperature to give crop A. The original filtrate was placed in a separatory funnel; the organic layer was separated, dried over magnesium sulfate and stripped to give crop B. The IR spectra confirmed that crops A and B were the same product. Crops A and B were combined to give 2.1 g of the above-identified product as a white solid, melting point 139°–141° C.

Elemental analysis for $C_{11}H_{13}Cl_4NO_4S_3$ showed: calculated %C 28.64, %H 2.84, and %N 3.04; found %C 29.73, %H 3.02 and %N 3.26.

Compounds made in accordance with Examples 1 to 18 are found in Tables I and II.

In addition, by following the procedures described in Examples 1 to 18 and using the appropriate starting materials, the following compounds are made:

N-methyl,N-(1,1,1,2-tetrachloroethylsulfenyl) 2-(methylsulfonyl)ethanesulfonamide;

N-methyl,N-(1,1,1,2-tetrachloroethylsulfenyl) 2-(tert-butylsulfonyl)ethanesulfonamide;

N-methyl,N-(trichlorovinylsulfenyl) 2-(methylsulfonyl)ethanesulfonamide;

N-methyl,N-(trichlorovinylsulfenyl) 2-(tert-butylsulfonyl)ethanesulfonamide;

N-methyl,N-(1,1,2,2-tetrachloroethylsulfenyl) 2-(ethylsulfonyl)ethanesulfonamide;

N-methyl,N-(1,1,2,2-tetrachloroethylsulfenyl) 2-(n-propylsulfonyl)ethanesulfonamide;

N-methyl,N-(1,1,2,2-tetrachloroethylsulfenyl) 2-(prop-2-enylsulfonyl)ethanesulfonamide;

N-methyl,N-(1,1,2,2-tetrachloroethylsulfenyl) 2-(n-butylsulfonyl)ethanesulfonamide;

N-methyl,N-(1,1,2,2-tetrachloroethylsulfenyl) 2-(n-but-2-enylsulfonyl)ethanesulfonamide;

N-methyl,N-trichloromethylsulfenyl (2-ethylsulfonyl)ethanesulfonamide;

N-methyl,N-trichloromethylsulfenyl (2-n-propylsulfonyl)ethanesulfonamide;

N-methyl,N-trichloromethylsulfenyl 2-(prop-2-enylsulfonyl)ethanesulfonamide;

N-methyl,N-trichloromethylsulfenyl 2-(n-butylsulfonyl)ethanesulfonamide;

N-methyl,N-trichloromethylsulfenyl) 2-(n-but-2-enyl-sulfonamide)ethanesulfonamide;
N-methyl,N-trichloromethylsulfenyl) 2-(prop-2-ynyl-sulfonyl)ethanesulfonamide;
N-methyl,N-(1,1,2,2-tetrachloroethylsulfenyl) 2-(prop-2-ynylsulfonyl)ethanesulfonamide;
N-methyl,N-(1-fluoro-1,1,2,2-tetrachloroethylsulfenyl) 2-(methylsulfonyl)ethanesulfonamide;
N-methyl,N-(1-fluoro-1,1,2,2-tetrachloroethylsulfenyl) 2-(tert-butylsulfonyl)ethanesulfonamide;
N-(prop-2-enyl), N-(1-fluoro-1,1,2,2-tetrachloroethyl-sulfenyl 2-(methylsulfonyl)ethanesulfonamide;
N-(prop-2-enyl), N-1,1,1,2-tetrachloroethylsulfenyl) 2-(methylsulfonyl)ethanesulfonamide, and
N-(prop-2-enyl), N-(trichlorovinylsulfenyl) 2-(methyl-sulfonyl)ethanesulfonamide.

EXAMPLE A

Mycelial Inhibition

The compound was evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium monilofroma, Botrytis cinerea* and *Aspergillus niger*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip in terms of mg/cm$^2$ needed for 99% control of the fungus (ED$_{99}$). The effectiveness of the compound for fungicidal activity is reported in Table III in terms of the percent of the ED$_{99}$ of the test compound of the ED$_{99}$ of the standard Difolatan ®.

EXAMPLE B

Bean Powdery Mildew

The compound was tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table III.

EXAMPLE C

Tomato Late Blight

The compound was tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table III.

EXAMPLE D

Celery Late Blight

The Celery Late Blight test was conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table III.

EXAMPLE E

Tomato Early Blight

The compound was tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table III.

Example F

Grape Downy Mildew

The compound was tested for the control of the Grape Downy Mildew organism, *Plasmopara viticola*. Seedlings of *Vitis vinifera* var. Emperor (7+weeks old) were used as hosts. The plants were sprayed with a 250 ppm solution of the test compound in an acetone and water solution containing a small amount of non-ionic emulsifier. The treated plants were inoculated one day later by spraying them with a spore suspension of the organism. The treated plants were then held in a greenhouse at a temperature of about 68° F. to about 72° F. (relative humidify varied between about 30 and about 99%) for 4 days. The plants were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table III.

Example G

Bean Rust

The compound was evaluated for their ability to eradicate Bean Rust caused by *Uromyces phaseoli tipica* on pinto beans.

Pinto bean plants variety Idaho 1-11, 16 (summer) or 19 (winter) days old were inoculated with a 50 ppm suspension of uredospores in water containing a small amount of non-ionic surfactant. The inoculated plants were placed in an environmental chamber immediately after inoculation and incubated 20 hours. Following the incubation period, the plants were removed from the chamber and placed in a greenhouse maintained at 66°–68° F. and 60–80% relative humidity. Two days after inoculation, the plants were treated by spraying with a 200 ppm solution of test compound in an acetone and water carrier formulation containing a small amount of non-ionic surfactant. One or two replicate pots (each containing two plants) were used for each compound. In addition, one or two replicate pots were sprayed with the same carrier formulation (without a test compound) as a control (hereinafter "untreated checks"). The plants were kept in the greenhouse until evaluated. The plants were evaluated for disease control when disease symptoms were well developed on the untreated checks, normally about 14 days after treatment. The percentage disease control (or eradication) provided by a test compound was based on the percent disease reduction relative to the untreated checks. The results are reported in Table III.

EXAMPLE H

Rice Blast

The compound was tested for control of the Rice Blast organism *Piricularia oryzae,* using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\%\ \text{Control} = 100 - 100 \times \left( \frac{\%\ \text{disease in treated plants}}{\%\ \text{disease in check}} \right)$$

The results are tabulated in Table III.

TABLE I

Compounds of the Formula:

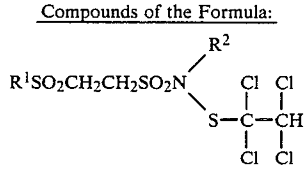

| | | | | ELEMENTAL ANALYSIS | | | | | |
|---|---|---|---|---|---|---|---|---|---|
| | | | | % C | | % H | | % N | |
| Compound | $R^1$ | $R^2$ | Physical State | Calc. | Found | Calc. | Found | Calc. | Found |
| 1 41942 | $CH_3$ | $-CH_3$ | white solid, mp 120–123° C. | 18.05 | 18.93 | 2.78 | 3.08 | 3.51 | 4.11 |
| 2 42428 | $CH_3$ | $-CH_2CH_3$ | off-white solid mp 119–120° C. | 20.35 | 21.26 | 3.17 | 3.41 | 3.39 | 3.59 |
| 3 42429 | $CH_3$ | $-CH_2CH_2CH_3$ | white solid, mp 72–73° C. | 22.49 | 23.52 | 3.54 | 3.97 | 3.28 | 3.38 |
| 4 41938 | $CH_3$ | $-CH(CH_3)_2$ | white solid, mp 141–143° C. | 22.49 | 23.35 | 3.54 | 3.8 | 3.28 | 3.64 |
| 5 41979 | $CH_3$ | $-C(CH_3)_3$ | white solid, mp 117–118° C. | 24.49 | 24.02 | 3.89 | 3.69 | 3.17 | 3.23 |
| 6 42096 | $CH_3$ | $-CH_2CH{=}CH_2$ | light yellow solid, mp 96–99° C. | 22.59 | 23.94 | 3.08 | 3.09 | 3.29 | 3.34 |
| 7 42203 | $CH_3$ | | solid, mp 154–156° C. | 28.64 | 29.12 | 2.84 | 2.83 | 3.04 | 3.45 |
| 8 42545 | $-CH_3$ | 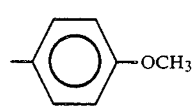  | white solid, mp 144–148° C. | 29.34 | 29.2 | 3.08 | 3.17 | 2.85 | 2.77 |
| 9 42595 | $-C(CH_3)_3$ | $-CH_3$ | white solid, mp 151–152° C. | 24.49 | 27.16 | 3.88 | 4.09 | 3.17 | 3.31 |
| 10 42201 | 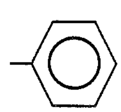  | $-CH_3$ | white solid, mp 139–141° C. | 28.64 | 29.73 | 2.84 | 3.02 | 3.04 | 3.26 |
| 11 42361 | 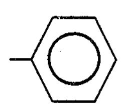  | $-CH_2CH_3$ | brown oil | 30.32 | 31.2 | 3.18 | 3.50 | 2.95 | 2.92 |

TABLE I-continued

Compounds of the Formula:

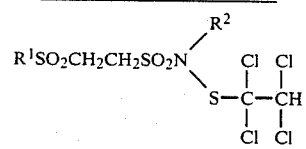

| Compound | R$^1$ | R$^2$ | Physical State | %C Calc. | %C Found | %H Calc. | %H Found | %N Calc. | %N Found |
|---|---|---|---|---|---|---|---|---|---|
| 12 42430 | C$_6$H$_5$— | —CH$_2$CH$_2$CH$_3$ | white solid, mp 88–90° C. (Dec) | 31.91 | 32.52 | 3.50 | 3.74 | 2.86 | 2.91 |
| 13 42255 | C$_6$H$_5$— | —CH(CH$_3$)$_2$ | white solid, mp 119–121° C. | 31.91 | 31.55 | 3.50 | 3.42 | 2.86 | 2.96 |
| 14 42360 | C$_6$H$_5$— | —C(CH$_3$)$_3$ | white solid, mp 131–132° C. | 33.41 | 34.4 | 3.80 | 4.25 | 2.78 | 2.91 |

TABLE II

Compounds of the Formula:

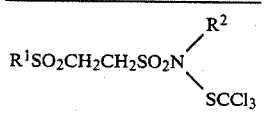

| Compound | R$^1$ | R$^2$ | Physical State | %C Calc. | %C Found | %H Calc. | %H Found | %N Calc. | %N Found |
|---|---|---|---|---|---|---|---|---|---|
| 15 41941 | —CH$_3$ | —CH$_3$ | white solid, mp 141–143° C. | 17.12 | 18.21 | 2.87 | 3.2 | 3.99 | 4.85 |
| 16 41939 | —CH$_3$ | —CH(CH$_3$)$_2$ | white solid, mp 154–156° C. | 22.20 | 23.71 | 3.73 | 4.05 | 3.70 | 4.06 |
| 17 41977 | —CH$_3$ | —C(CH$_3$)$_3$ | white solid, mp 105–106° C. | 24.46 | 23.44 | 4.11 | 4.02 | 3.57 | 3.76 |
| 18 42194 | —CH$_3$ | C$_6$H$_5$— | white solid, mp 185–187° C. (Dec) | 29.09 | 28.50 | 2.93 | 2.93 | 3.39 | 3.62 |
| 19 42546 | —CH$_3$ | —C$_6$H$_4$—OCH$_3$ | white solid, mp 146–149° C. | 29.84 | 29.73 | 3.19 | 3.31 | 3.16 | 3.08 |
| 20 42594 | —C(CH$_3$)$_3$ | —CH$_3$ | white solid, mp 178–179° C. | 24.46 | 26.39 | 4.11 | 4.7 | 3.57 | 3.56 |
| 21 42202 | C$_6$H$_5$— | —CH$_3$ | white solid, mp 156–157° C. (Dec) | 29.09 | 29.2 | 2.93 | 3.25 | 3.39 | 3.65 |
| 22 42431 | C$_6$H$_5$— | —CH$_2$CH$_3$ | white solid, mp 120–121° C. | 30.96 | 31.12 | 3.31 | 3.31 | 3.28 | 3.36 |

TABLE II-continued

Compounds of the Formula:

$$R^1SO_2CH_2CH_2SO_2N\begin{matrix}R^2\\SCCl_3\end{matrix}$$

| Compound | $R^1$ | $R^2$ | Physical State | %C Calc. | %C Found | %H Calc. | %H Found | %N Calc. | %N Found |
|---|---|---|---|---|---|---|---|---|---|
| 23 42432 | phenyl | —CH$_2$CH$_2$CH$_3$ | white solid, mp 110–112° C. | 32.69 | 30.09 | 3.66 | 3.42 | 3.18 | 3.01 |
| 24 42256 | phenyl | —CH(CH$_3$)$_2$ | white solid, mp 110–112° C. | 32.69 | 33.84 | 3.66 | 3.68 | 3.18 | 3.6 |
| 25 42257 | phenyl | —C(CH$_3$)$_3$ | white solid, mp 127–129° C. | 34.33 | 34.23 | 3.99 | 4.03 | 3.08 | 3.19 |

TABLE III

| Compound | Mycelial Inhibition Phy. | Rhiz. | Fusar. | Botr. | Aspen | GDM | TLB | RB | TLB | CLB | BPM | BR |
|---|---|---|---|---|---|---|---|---|---|---|---|---|
| 1 41942 | 348 | 114 | 100 | 100 | 100 | 97 | 87 | 80 | — | 100 | 70 | 8 |
| 2 42428 | — | 58 | 38 | 43 | 0 | 60 | 36 | 70 | 0 | 83 | 0 | 0 |
| 3 42429 | — | 67 | 38 | 43 | 67 | 93 | 57 | 90 | 0 | 92 | 0 | 0 |
| 4 41938 | 43 | 114 | 0 | 100 | 77 | 33 | 20 | 96 | — | 22 | 0 | 0 |
| 5 41979 | 0 | 0 | 0 | 0 | 0 | 79 | 36 | 90 | 0 | 0 | 0 | 0 |
| 6 42096 | 61 | 23 | — | 80 | — | 100 | 83 | 50 | 75 | 33 | 0 | 0 |
| 7 42203 | 0 | 13 | 0 | 0 | 0 | 100 | 92 | 97 | 95 | 83 | 0 | 0 |
| 8 42545 | 50 | 28 | 39 | 33 | 0 | 86 | 97 | 40 | 86 | 58 | 0 | 0 |
| 9 42595 | 100 | 92 | 51 | 49 | 62 | 93 | 97 | 18 | 88 | 94 | 17 | 0 |
| 10 42201 | 14 | 28 | 77 | 32 | 0 | 100 | 62 | 97 | 95 | 42 | 0 | 0 |
| 11 42361 | 0 | 0 | 0 | 0 | 0 | 0 | 0 | 0 | 25 | 8 | 53 | 0 |
| 12 42430 | — | 58 | 38 | 43 | 0 | 93 | 14 | 80 | 20 | 83 | 0 | 0 |
| 13 42255 | 14 | 100 | — | 40 | 88 | 62 | 0 | 64 | — | 15 | 0 | 0 |
| 14 42360 | 0 | 88 | 0 | 0 | 0 | 15 | 0 | 10 | 25 | 0 | 27 | 7 |
| 15 41941 | 0 | 0 | 0 | 0 | 0 | 33 | 20 | 70 | — | 0 | 0 | 8 |
| 16 41939 | 0 | 0 | 0 | 0 | 0 | 60 | 80 | 90 | — | 44 | 0 | 0 |
| 17 41977 | 0 | 0 | 0 | 0 | 0 | 0 | 0 | 0 | 43 | 0 | 0 | 0 |
| 18 42194 | 0 | 0 | 0 | 0 | 0 | 93 | 8 | 92 | 88 | 17 | 0 | 0 |
| 19 42546 | 25 | 20 | 0 | 0 | 0 | 71 | 83 | 0 | 14 | 8 | 17 | 0 |
| 20 42594 | 15 | 0 | 0 | 0 | 0 | 80 | 93 | 18 | 25 | 17 | 0 | 0 |
| 21 42202 | 0 | 0 | 0 | 0 | 0 | 93 | 54 | 83 | 88 | 42 | 0 | 0 |
| 22 42431 | — | 0 | 0 | 0 | 0 | 73 | 14 | 30 | 0 | 58 | 0 | 0 |
| 23 42432 | — | 0 | 0 | 0 | 0 | 80 | 7 | 10 | 20 | 58 | 8 | 0 |
| 24 42256 | 0 | 0 | 0 | 0 | 0 | 37 | 0 | 55 | — | 23 | 0 | 0 |
| 25 42257 | 0 | 0 | 0 | 0 | 0 | 0 | 0 | 9 | — | 0 | 0 | 0 |

Pyth. = *Pythium ultimum*
Rhiz. = *Rhizoctonia solani*
Fusar. = *Fusarium monilofroma*
Botr. = *Botrytis cinerea*
Asper. = *Aspergillus niger*
GDM = Grape Downy Mildew
TLB = Tomato Late Blight
CLB = Celery Late Blight
TEB = Tomato Early Blight
BR = Bean Rust Eradicant
BPM = Bean Powdery Mildew
RB = Rice Blast

What is claimed is:

1. A compound of the formula:

$$R^1-SO_2CH_2CH_2SO_2N\begin{matrix}R^2\\S-R^3\end{matrix}$$

wherein
$R^1$ is lower alkyl, lower alkenyl, lower alkynyl or aryl of 6 to 10 carbon atoms optionally substituted with up to 3 halogen atoms;
$R^2$ is lower alkyl, lower alkenyl, lower alkynyl or aryl of 6 to 10 carbon atoms optionally substituted with up to 3 halogen atoms or up to 3 lower alkoxy groups; and $R^3$ is alkyl of 1 to 3 carbon atoms substituted with 3 to 6 halogen atoms or trihalovinyl.

2. A compound according to claim 1 wherein $R^1$ is lower alkyl or aryl; $R^2$ is lower alkyl, lower alkenyl or aryl.

3. A compound according to claim 2 wherein the halogen $R^3$ is substituted with is chlorine.

4. A compound according to claim 2 wherein $R^3$ is —$CCl_3$ or —$CCl_2CCl_2H$.

5. A compound according to claim 2 wherein $R^2$ is methyl or phenyl.

6. A compound according to claim 5 wherein $R^1$ is methyl.

7. A compound according to claim 6 wherein $R^2$ is methyl and $R^3$ is —$CCl_2CCl_2H$.

8. A compound according to claim 5 wherein $R^1$ is tert-butyl, $R^2$ is methyl and $R^3$ is —$CCl_2CCl_2H$.

9. A compound according to claim 1 wherein $R^3$ is tetrachloroethyl, trichloromethyl, trichlorovinyl, and 1-fluoro-1,1,2,2-tetrachloroethyl.

10. A method of controlling fungi which comprises contacting said fungi or their growth environment with a fungicidally effective amount of a compound of claim 1.

11. A method of controlling fungi which comprises contacting said fungi or their growth environment with a fungicidally effective amount of a compound of claim 2.

12. A method of controlling fungi which comprises contacting said fungi or their growth environment with a fungicidally effective amount of a compound of claim 4.

13. A method of controlling fungi which comprises contacting said fungi or their growth environment with a fungicidally effective amount of a compound of claim 7.

14. A method of controlling fungi which comprises contacting said fungi or their growth environment with a fungicidally effective amount of a compound of claim 8.

15. A method of controlling fungi which comprises contacting said fungi or their growth environment with a fungicidally effective amount of a compound of claim 9.

16. A fungicidal composition which comprises an inert carrier and a fungicidally effective amount of a compound of claim 1.

17. A fungicidal composition which comprises an inert carrier and a fungicidally effective amount of a compound of claim 2.

18. A fungicidal composition which comprises an inert carrier and a fungicidally effective amount of a compound of claim 4.

19. A fungicidal composition which comprises an inert carrier and a fungicidally effective amount of a compound of claim 7.

20. A fungicidal composition which comprises an inert carrier and a fungicidally effective amount of a compound of claim 8.

21. A fungicidal composition which comprises an inert carrier and a fungicidally effective amount of a compound of claim 9.

* * * * *